US00PP37674P3

(12) United States Plant Patent
Whitaker et al.

(10) Patent No.: US PP37,674 P3
(45) **Date of Patent: *Sep. 8, 2026**

(54) STRAWBERRY PLANT NAMED 'FL 19.66-220'

(50) Latin Name: ***Fragaria* X *ananassa* Duchesne**
Varietal Denomination: FL 19.66-220

(71) Applicants: Florida Foundation Seed Producers, Inc., Marianna, FL (US); University of Florida Research Foundation, Inc., Gainesville, FL (US)

(72) Inventors: Vance M. Whitaker, Brandon, FL (US); Cheryl Dalid, Valrico, FL (US); Luis Osorio, Tampa, FL (US)

(73) Assignees: Florida Foundation Seed Producers, Inc., Marianna, FL (US); University of Florida Research Foundation, Inc., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/896,723

(22) Filed: Sep. 25, 2024

(65) Prior Publication Data

US 2026/0090487 P1 Mar. 26, 2026

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208, 209
CPC ..... A01H 5/0893
See application file for complete search history.

(56) References Cited

U.S. PATENT DOCUMENTS

| | | | |
|---|---|---|---|
| PP30,564 | P3 | 6/2019 | Whitaker |
| PP33,451 | P2 | 9/2021 | Whitaker |
| PP33,477 | P2 | 9/2021 | Whitaker |
| PP35,802 | P2 | 5/2024 | Whitaker |

OTHER PUBLICATIONS

U.S. Appl. No. 18/896,542, filed Sep. 25, 2024, Whitaker.

*Primary Examiner* — Kent L Bell
(74) *Attorney, Agent, or Firm* — Dentons US LLP

(57) ABSTRACT

A new and distinct variety of strawberry (*Fragaria* X *ananassa*), which originated from seed produced by a hand-pollinated cross between 'FL 16.30-128' and 'FL 17.66-44'. The new strawberry, named 'FL 19.66-220', can be distinguished at least by its white internal fruit color when fully ripe; white external fruit color with a pink blush and red achenes when fully ripe; conical shape; and high soluble solids content when grown in West Central Florida or other regions that have a climate similar to that of West Central Florida.

1 Drawing Sheet

Latin name of the genus and species of the plant claimed: *Fragaria* X *ananassa* Duchesne.

Variety denomination: 'FL 19.66-220'.

BACKGROUND OF THE INVENTION

The present invention relates to a new and distinct variety of strawberry plant (*Fragaria* X *ananassa* Duchesne) named 'FL 19.66-220'. This new strawberry plant is distinguished at least by its ability to produce fruit that have white internal color and white external color with a pink blush when fully ripe, consistent conical shape, and a sweet flavor including high soluble solids content when grown in West Central Florida. Asexual propagation of 'FL 19.66-220' was performed at Balm, Florida, which is also where the selection was made and the plants were tested. 'FL 19.66-220' can be contrasted with 'Florida Brilliance' (U.S. Plant Pat. No. 30,564), the current leading red-fruited strawberry variety in Hillsborough County and 'FL 18.52-66' (U.S. Plant Pat. No. 35,802), the current leading white-fruited strawberry variety grown commercially in the region. 'FL 19.66-220' is a promising candidate for commercial success because it produces sweet-tasting fruit that are white with light pink blush and red achenes when fully ripe throughout the entire Florida market window.

SUMMARY OF THE INVENTION

'FL 19.66-220', when grown in a subtropical climate during the fall, winter, or a combination thereof, can be distinguished from all other strawberry plants, known by the Inventors, by at least the following characteristics: white internal fruit color when fully ripe; white external fruit color with a pink blush and red achenes when fully ripe; conical shape; and high soluble solids content.

'FL 19.66-220' originated in a strawberry breeding plot in Balm, Florida. The seed parent was 'FL 16.30-128' (U.S. Plant Pat. No. 33,451), a patented cultivar with high fruit firmness, conical shape and high soluble solids. The pollen parent was 'FL 17.66-44', an unreleased, unpatented breeding selection with white internal color and white to light pink external color when ripe. The seeds resulting from the controlled hybridization were germinated in a greenhouse, and the resulting seedlings were planted and allowed to produce daughter plants by asexual propagation (i.e. by runners). Two daughter plants from each seedling were transplanted to raised beds, where they fruited. 'FL 19.66-220' was selection number 220 of the 66$^{th}$ cross in the 2019-2020 seedling trial, and thus was given the breeding trial designation of 'FL 19.66-220'. 'FL 19.66-220' exhibited unique white fruit color with a pink blush when fully-ripe, excellent shape and sweet flavor characterized with high soluble solids. 'FL 19.66-220' has been asexually propagated annually by runners; and test plantings have established that the vegetative and fruit characteristics of the propagules are identical to those of the initial daughter plants.

'FL 19.66-220' can be distinguished from its seed parent 'FL 16.30-128' at least by its white fruit color with red achenes as compared with the red fruit color and yellow achenes of the seed parent. 'FL 19.66-220' can also be distinguished from its pollen parent 'FL 17.66-44' at least by its 15% greater fruit size and 20% greater firmness.

Currently, 'Florida Brilliance' (U.S. Plant Pat. No. 30,564) is the dominant strawberry variety in Hillsborough County, Florida. 'FL 19.66-220' can be distinguished from 'Florida Brilliance' due to its white fruit color with a pink blush when fully ripe (FIG. 1) as compared to the medium red fruit color of 'Florida Brilliance'. 'FL 19.66-220' can be distinguished from 'FL 18.52-66' by its 10-32% greater soluble solids content than 'FL 18.52-66' (Table 1) leading to a uniquely sweet flavor. Additionally, 'FL 19.66-220' can also be distinguished from 'FL 16.78-109' (U.S. Plant Pat. No. 33,477), another variety which exhibits white internal fruit color and white to light pink external fruit color when fully ripe, at least by its petiole color, typical anthocyanin presence on the stipule, and absence of anthocyanin presence on the stolons.

'FL 19.66-220' is more resistant to Colletotrichum crown rot (caused by *Colletotrichum gloeosporioides*) than both commercial standards.

BRIEF DESCRIPTION OF THE DRAWINGS

'FL 19.66-220' is illustrated by the accompanying photographs of 5-month-old specimens taken in February 2021. The colors shown are as true as can be reasonably captured by conventional photographic procedures.

FIG. 1. Shows unripe and ripe fruit with white flesh with a pink blush and red achenes from 5-month-old specimens in March, 2024 near Balm, FL.

DETAILED BOTANICAL DESCRIPTION

The following detailed botanical description sets forth the distinctive characteristics of 'FL 19.66-220'. The present botanical description is of 'FL 19.66-220' when grown under the ecological conditions that prevail during the winter production season in Balm, Florida, i.e., warm days and cool nights. Colors are objectively described using the CIELAB color scale (originally published by the International Commission on Illumination (CIE) in 1976) as measured using a Minolta Chroma Meter CR-400 (Minolta, Ramsey, NJ) colorimeter with a 1 cm aperture, calibrated against a white tile (Y=85.5, x=0.3164, y=0.3237). When the CIELAB color designations differ from the accompanying photographs, the CIELAB color designations are accurate.

Phenotypic Description of *Fragaria* X *ananassa* Duchesne 'FL 19.66-220'

Classification:
- *Botanical.*—*Fragaria* X *ananassa* Duchesne.
- *Common name.*—Strawberry.

Parentage:
- *Seed parent.*—'FL 16.30-128'.
- *Pollen parent.*—'FL 17.66-44'.

Plant:
- *Average height.*—19 cm to 25 cm.
- *Average width.*—21 cm to 30 cm.
- *Growth habit.*—Compact, round.
- *Number of crowns per plant.*—4 to 6 depending on seasonal conditions.
- *Vigor.*—Low.

Leaf:
- *Overall description.*—Pinnately compound with three leaflets.

Petiole:
- *Average length.*—14.5 cm.
- *Average diameter.*—1.5 mm.
- *Pubescence.*—Light.
- *Pubescence density.*—Light to Med.
- *Pose of hairs.*—Perpendicular.
- *Texture.*—Smooth.
- *Anthocyanin presence.*—Absent.
- *Color.*—Pale green (L*=63.12, a*=−15.53, b*=33.80).

Petiolule:
- *Length.*—Terminal leaflet: 5.1 mm. Lateral leaflets: 4.5 mm.
- *Diameter.*—1.9-2.1 mm.
- *Color.*—Light green (L*=44.62, a*=−8.07, b*=23.12).
- *Texture.*—Smooth.

Stipule:
- *Length.*—28.6 mm to 30 mm.
- *Width.*—14-16 mm along the base of the petiole attachment.
- *Anthocyanin presence.*—Occasional.
- *Color.*—Light green (L*=77.87, a*=−5.21, b*=16.60).
- *Texture.*—Smooth.

Terminal leaflet:
- *Average length.*—66 mm.
- *Average breadth.*—56 mm.
- *Length/width ratio.*—1.07.
- *Shape in cross section.*—Concave.
- *Color, upper surface.*—Medium green (L*=40.11, a*=−17.09, b*=23.53).
- *Color, lower surface.*—Light green (L*=55.27, a*=−12.28, b*=16.75).
- *Glossiness.*—Low gloss.
- *Leaflet shape.*—Obovate.
- *Base shape.*—Cuneate.
- *Apex descriptor.*—Rounded.
- *Pubescence density.*—Sparse.
- *Texture* (*upper surface*).—Moderately smooth.
- *Texture* (*lower surface*).—Moderately smooth.
- *Venation pattern.*—Pinnate.

Secondary leaflets:
- *Average length.*—57 mm.
- *Average breadth.*—52 mm.
- *Length/width ratio.*—1.1.
- *Shape in cross section.*—Slightly concave.
- *Color, upper surface.*—Medium green (L*=36.27, a*=−15.08, b*=19.26).
- *Color, lower surface.*—Light green (L*=52.30, a*=−14.79, b*=23.00).
- *Glossiness.*—Slight gloss.
- *Leaflet shape.*—Obovate.
- *Base shape.*—Oblique rounded.

*Apex descriptor*.—Obtuse to rounded.
*Pubescence density*.—Sparse.
*Texture* (*upper surface*).—Moderately smooth.
*Texture* (*lower surface*).—Moderately smooth.
*Venation pattern*.—Pinnate.

Leaflet margins: Crenate, with an average of 22 and 22 serrations per terminal and secondary leaflet, respectively.

Stolons:
*Number of daughter plants*.—20 to 35 depending on environmental conditions.
*Anthocyanin presence*.—Absent.
*Thickness*.—1.8 mm to 2.3 mm.
*Pubescence*.—Light.

Inflorescence:
*Time of flowering*.—Partial remontancy, commencing two weeks after establishment and continually thereafter in suitable climate.
*Flower number per plant*.—35 to 50 flowers over a 4 month Florida growing season.
*Flower height*.—0 to 15 cm above soil surface depending on angle of pedicel.
*Position relative to canopy*.—Flowers open at or significantly below canopy height.
*Branching of the inflorescence*.—At or within 3 cm of the crown.

Petals:
*Number*.—5.
*Length*.—12 mm.
*Width*.—11 mm.
*Shape*.—Orbicular.
*Apex*.—Rounded.
*Base*.—Rounded.
*Margin*.—Smooth.
*Average diameter of the corolla* (*i.e. the petals collectively*).—32 mm.
*Average number of stamens*.—24-26.
*Color* (*upper surface*).—White (L*=83.91, a*=−2.05, b*=7.56).
*Color* (*lower surface*).—White (L*=84.10, a*=−2.09, b*=7.55).

Calyx:
*Diameter*.—33 mm.
*Diameter of calyx relative to corolla*.—1.1.
*Diameter of calyx relative to the fruit*.—0.9.
*Insertion of calyx*.—Level to slightly inserted.
*Color*.—Medium green (L*=52.00, a*=−13.57, b*=34.02).

Sepals:
*Number per flower*.—12-13.
*Length*.—12 mm to 15 mm.
*Width*.—8 mm to 10 mm.
*Apex*.—variable, rounded to acute.
*Margin*.—Smooth.
*Shape*.—Lanceolate and sometimes lobed.
*Color, upper surface*.—Medium green (L*=42.61, a*=−13.17, b*=23.25).
*Color, lower surface*.—Light green (L*=50.28, a*=−9.83, b*=21.68).

Pedicels: Attached to mature primary fruit and 10 cm to 15 cm in length and 1.8 to 2.0 mm in diameter depending on the time of the season. At peak production, the plant will have several crowns, each producing a truss. Each truss will have 5 to 8 pedicels. Inflorescences branch very close to the crown, rendering the peduncle rarely visible.

Fruit:
*Number per truss*.—5 to 8.
*Shape*.—Conical.
*Average fruit weight*.—23 to 27 g.
*Weight, primary fruit*.—21 to 32 g.
*Weight, secondary and tertiary fruit*.—13 to 19 g.
*Length, primary fruit*.—42 mm to 52 mm.
*Width, primary fruit*.—30 mm to 39 mm.
*Fruit flavor*.—Sweet.
*Fruit soluble solids content* (*brix*).—As high as 10.81% in January 2022 (Table 1).
*Fruit cavity*.—Rare.
*Achenes*.—Slightly sunken, 70 to 160 per fruit, at least 55% of which are red in color; 45% are yellow or green.
*External fruit color*.—White with light pink blush (a*=8.75).
*Internal fruit color*.—White (a*=−1.42).
*Evenness of color*.—Pink blush on sun side, majority of achenes red in color.
*Flesh and skin firmness at full ripe stage*.—Very firm.
*Rain damage*.—Similar or improved as compared to 'FL 16.78-109' (U.S. Plant Pat. No. 33,477).

Yield: 21% to 32% lower than 'FL 18.52-66'.

Preferred planting period: October 1$^{st}$ to October 10$^{th}$ in West Central Florida.

Nursery performance: 'FL 19.66-220' produces similar numbers of runners to 'Florida Brilliance'.

Disease resistance:
*Botrytis fruit rot* (*caused by Botrytis cinerea*).—Moderately susceptible.
*Powdery mildew* (*caused by Podosphaera aphanis*).—Moderately susceptible.
*Anthracnose fruit rot* (*caused by Colletotrichum acutatum*).—Susceptible.
*Charcoal rot* (*caused by Macrophomina phaseolina*).—Moderately resistant.

TABLE 1

Soluble solids content (SSC), pH, titratable acidity (TA) and SSC/TA from five harvests dates.

| Cultivar | SSC (%) | pH | TA (%) | SSC/TA |
|---|---|---|---|---|
| January 2022 | | | | |
| 'Florida Brilliance' | 8.84 b[z] | 3.65 b | 0.82 a | 10.90 b |
| 'FL Pearl 66' | 9.57 ab | 3.71 b | 0.81 a | 11.88 ab |
| 'FL 19.66-220' | 10.81 a | 3.79 a | 0.75 a | 14.47 a |
| February 2022 | | | | |
| 'Florida Brilliance' | 7.68 b | 3.76 a | 0.63 b | 12.19 a |
| 'FL Pearl 66' | 8.41 ab | 3.67 b | 0.76 ab | 11.17 a |
| 'FL 19.66-220' | 9.23 a | 3.72 ab | 0.79 a | 11.68 a |
| March 2022 | | | | |
| 'Florida Brilliance' | 5.81 b | 3.83 a | 0.60 a | 9.77 b |
| 'FL Pearl 66' | 5.61 b | 3.81 a | 0.45 b | 12.64 a |
| 'FL 19.66-220' | 7.39 a | 3.80 a | 0.52 ab | 14.75 a |

TABLE 1-continued

Soluble solids content (SSC), pH, titratable acidity (TA) and SSC/TA from five harvests dates.

| Cultivar | SSC (%) | pH | TA (%) | SSC/TA |
|---|---|---|---|---|
| February 2024 | | | | |
| 'Florida Brilliance' | 6.96 c | 3.71 b | 0.74 a | 9.56 b |
| 'FL Pearl 66' | 7.85 b | 3.69 b | 0.72 a | 10.98 b |
| 'FL 19.66-220' | 8.90 a | 3.80 a | 0.67 a | 13.20 a |
| March 2024 | | | | |
| 'Florida Brilliance' | 6.07 c | 3.71 a | 0.69 c | 8.77 a |
| 'FL Pearl 66' | 6.81 b | 3.68 a | 0.79 b | 8.67 a |
| 'FL 19.66-220' | 8.50 a | 3.69 a | 0.90 a | 9.47 a |

[z]Mean separations within harvest dates and columns are by Tukey's HSD test, $P \leq 0.05$

What is claimed is:

1. A new and distinct strawberry plant named 'FL 19.66-220' as illustrated and described herein.

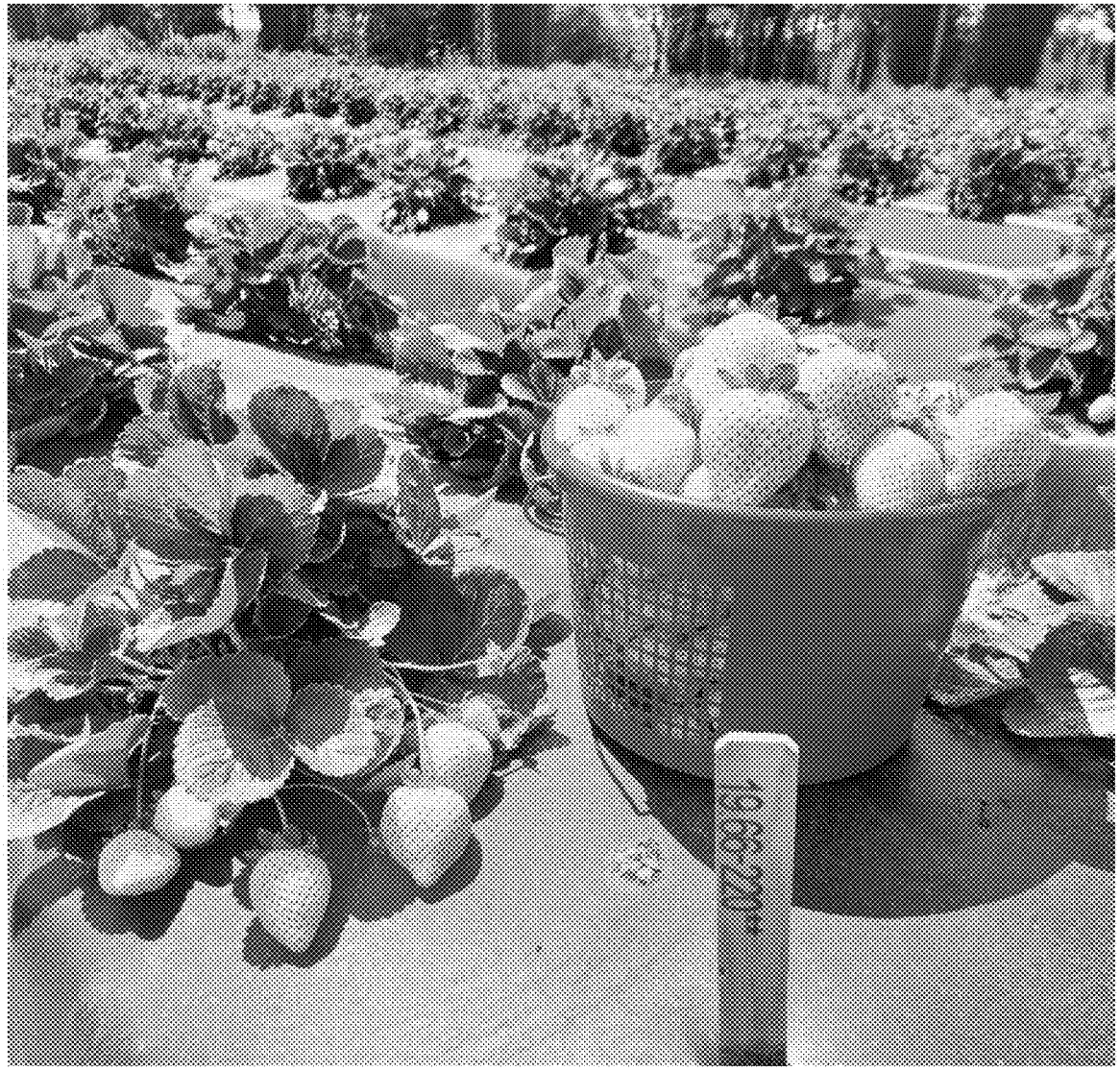

* * * * *